(12) United States Patent
Vander Meulen et al.

(10) Patent No.: US 8,034,116 B2
(45) Date of Patent: Oct. 11, 2011

(54) PROSTHETIC IMPLANT AND ASSEMBLY METHOD

(75) Inventors: Steve Vander Meulen, Leander, TX (US); Jerome J. Klawitter, Austin, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 195 days.

(21) Appl. No.: 12/233,976

(22) Filed: Sep. 19, 2008

(65) Prior Publication Data
US 2009/0240336 A1 Sep. 24, 2009

Related U.S. Application Data

(63) Continuation of application No. PCT/US2007/064594, filed on Mar. 22, 2007.

(60) Provisional application No. 60/743,661, filed on Mar. 22, 2006.

(51) Int. Cl.
*A61F 2/32* (2006.01)

(52) U.S. Cl. ............... 623/22.43; 623/23.51; 623/20.34; 623/18.11; 623/23.33

(58) Field of Classification Search ............... 623/18.11, 623/20.11, 21.11, 23.12, 23.14, 23.51, 20.34, 623/20.36, 22.43, 23.15, 23.33, 22.21, 22.4
See application file for complete search history.

(56) References Cited

U.S. PATENT DOCUMENTS

| | | |
|---|---|---|
| 3,707,006 A | 12/1972 | Bokros et al. |
| 4,183,104 A * | 1/1980 | Frey ............... 623/23.4 |
| 4,241,463 A | 12/1980 | Khovaylo |
| 4,279,041 A | 7/1981 | Buchholz |
| 4,289,244 A | 9/1981 | Frankhouser et al. |
| 4,770,658 A | 9/1988 | Geremakis |
| 4,795,468 A | 1/1989 | Hodorek et al. |
| 4,936,855 A | 6/1990 | Sherman |
| 4,955,916 A | 9/1990 | Carignan et al. |
| 4,997,445 A | 3/1991 | Hodorek |
| 5,062,853 A | 11/1991 | Forte |
| 5,507,826 A | 4/1996 | Besselink et al. |
| 5,593,445 A | 1/1997 | Waits |
| 6,916,342 B2 | 7/2005 | Frederick et al. |
| 6,997,958 B2 | 2/2006 | Hassler et al. |

(Continued)

FOREIGN PATENT DOCUMENTS

EP 0 524 874 7/1992

(Continued)

*Primary Examiner* — David Isabella
*Assistant Examiner* — Seema Swaminathan
(74) *Attorney, Agent, or Firm* — Fitch Even Tabin & Flannery

(57) ABSTRACT

An orthopedic prosthetic implant comprises a metal alloy stem element (13, 63, 113), which has one end portion (19, 69, 119) constructed to reside in the medullary cavity of a bone and an integral connector (23, 73, 123) at the opposite end to which crystalline brittle head (17, 67, 117), preferably made of pyrocarbon-coated graphite, is joined. The head interfaces with human bone, and its effective joinder to the stem element is achieved through a polymeric insert (15, 65, 115) of proportional shape and design which has selected elastic properties. The design and material of the polymeric insert allow it to be securely received within an interior cavity (35, 77, 131) of the pyrocarbon-coated graphite head and mated to the stem connector in an either rigidly or bi-polar arrangement. The method of joinder allows the construction of composite implants that utilize the most desirable properties of metallic and brittle crystalline materials.

14 Claims, 5 Drawing Sheets

| U.S. PATENT DOCUMENTS | | | | FOREIGN PATENT DOCUMENTS | | |
|---|---|---|---|---|---|---|
| 7,160,332 B2 | 1/2007 | Frederick et al. | EP | 1 632 200 | 8/2005 |
| 2003/0187512 A1 | 10/2003 | Frederick et al. | FR | 2 511 240 | 8/1982 |
| 2005/0033426 A1 | 2/2005 | Ogilvie et al. | FR | 2 686 252 | 1/1992 |
| 2005/0236741 A1 | 10/2005 | Arkenau et al. | | | |

* cited by examiner

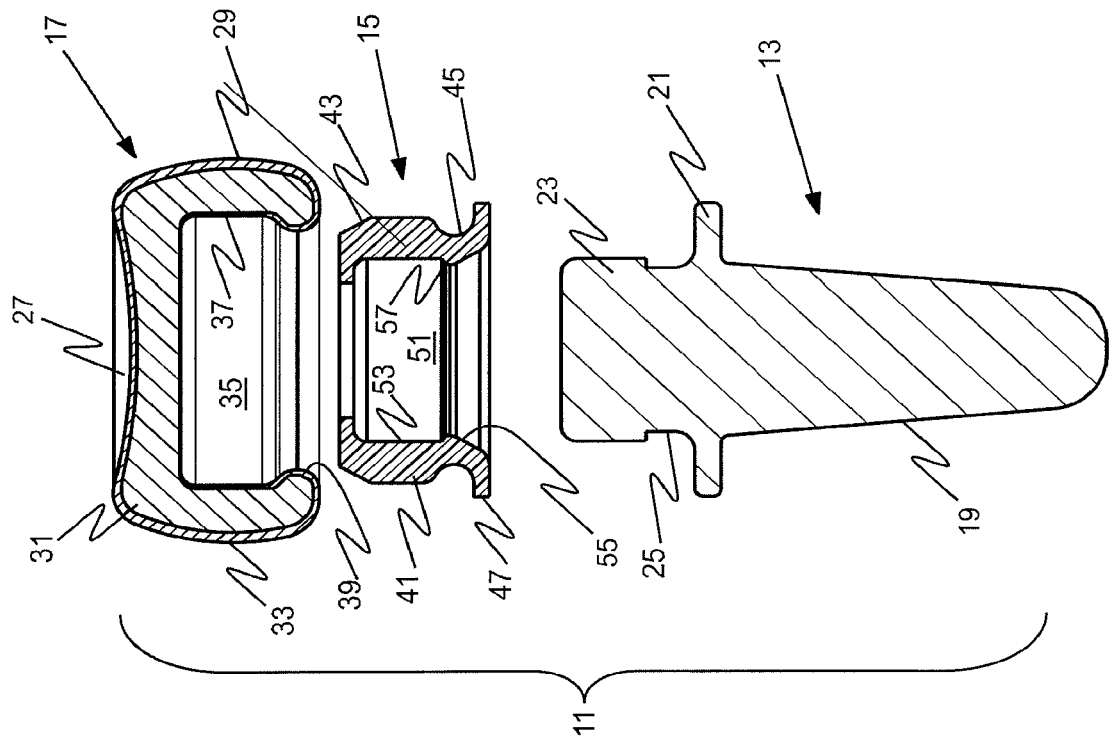
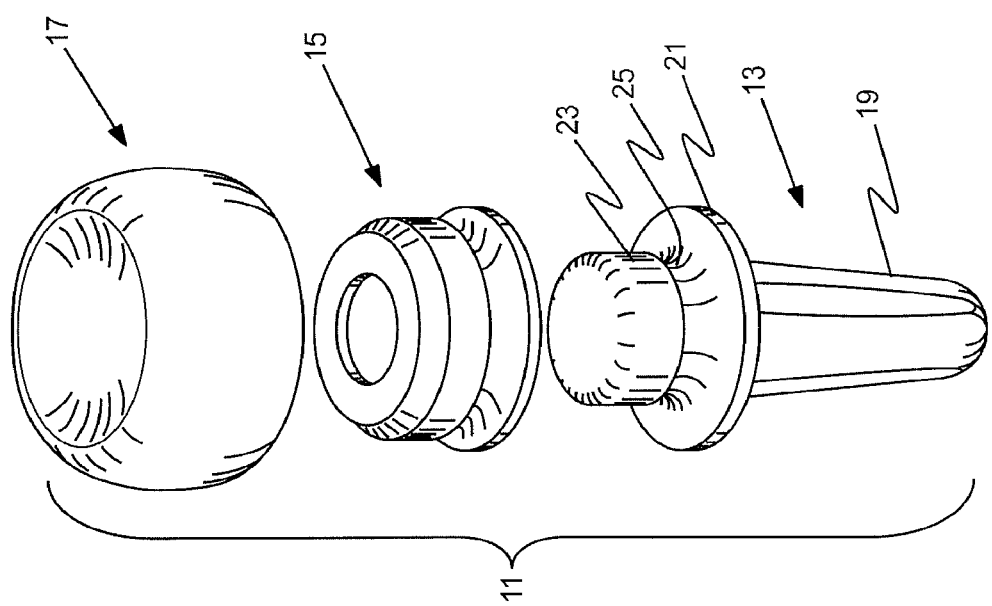

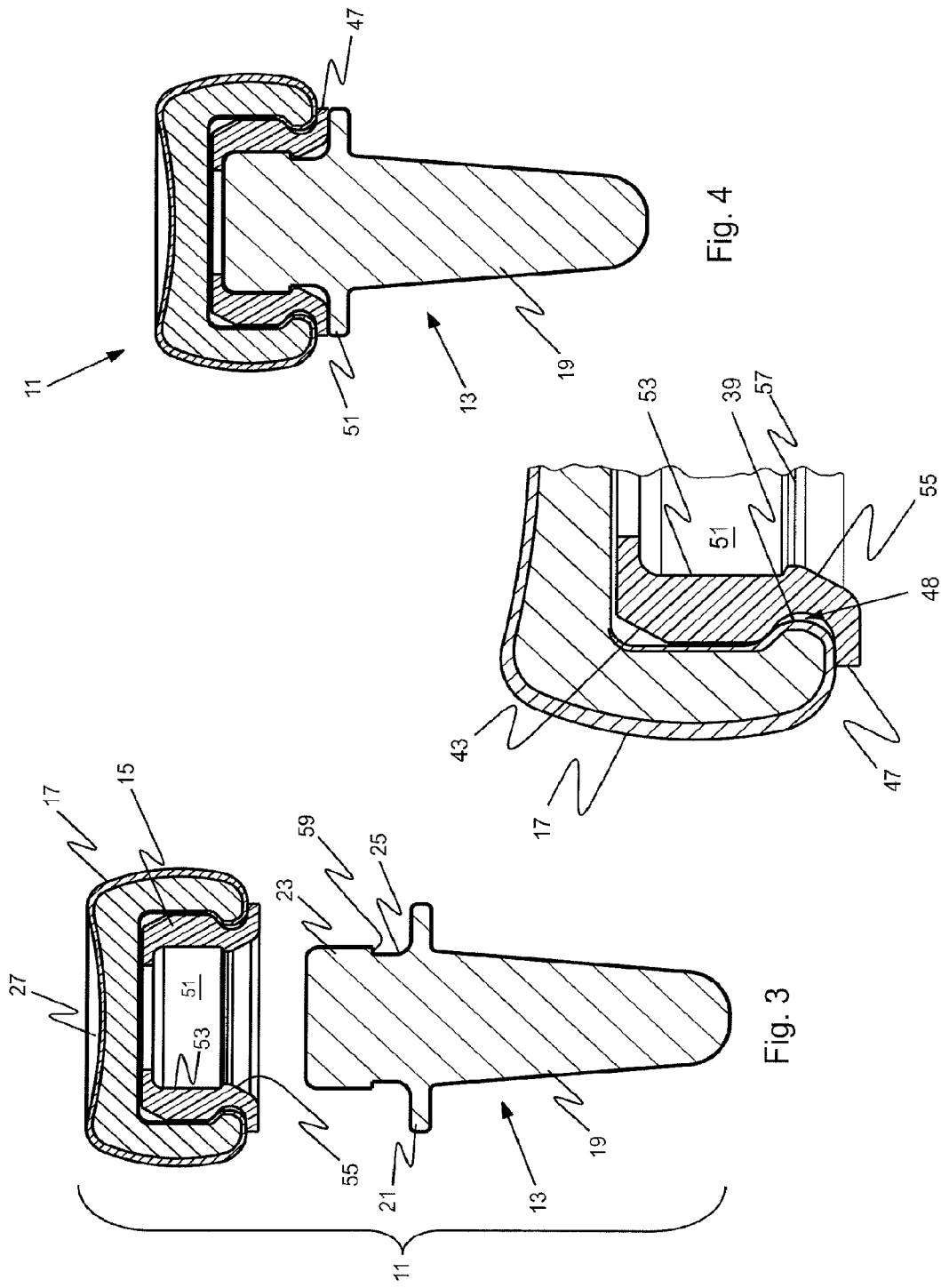

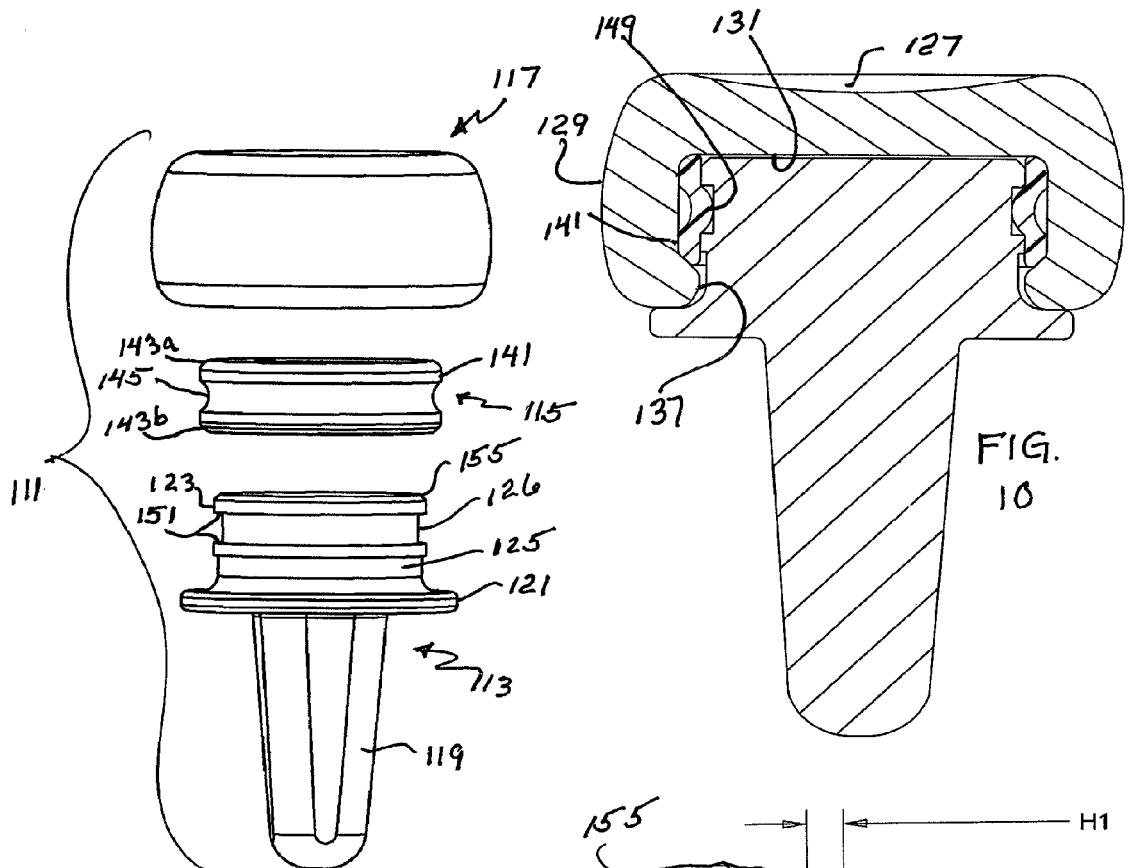
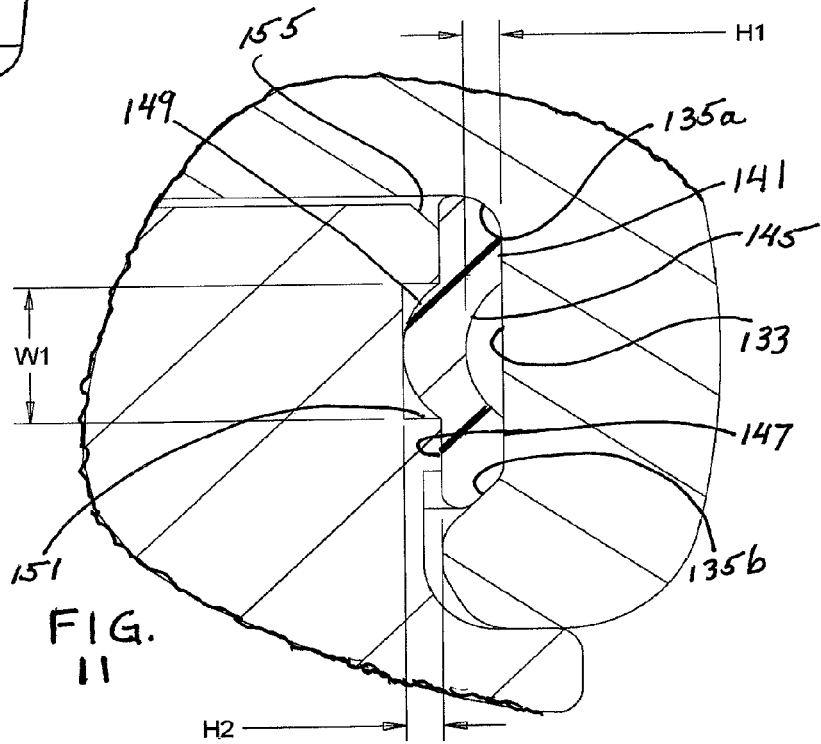
FIG. 9
FIG. 10
FIG. 11

PROSTHETIC IMPLANT AND ASSEMBLY METHOD

This application is a continuation of International Application No. PCT/US07/64594, filed 22 Mar. 2007, which claims priority from U.S. Provisional Application Ser. No. 60/743,661, filed Mar. 22, 2006, the disclosures of both of which are incorporated herein by reference.

This invention relates to prosthetic bone implants, and more particularly to a prosthetic bone implant to be used at a biological joint, and to methods for making such implants. Still more particularly, the invention relates to a prosthetic implant wherein a metal stem is joined to a head made of brittle crystalline material and to such assembly methods.

BACKGROUND OF THE INVENTION

The field of prosthetic implants to treat conditions of fracture, arthritis and other such conditions has grown greatly in the past 2-3 decades, and much work continues in these areas. Pyrocarbon-coated graphite materials have proved to be extremely wear-resistant and biocompatible, and they have become the materials of choice for certain applications where strength and other parameters can be met. U.S. Pat. Nos. 5,645,605, 6,159,247, 6,217,616, and 6,699,292 and Published Patent Application No. 2005/0033426 are examples of prosthetic implants that can be used at biological joints in the human body or the like. Although these patents illustrate the use of integral structures for such implants, there is also interest in constructing bone implants, particularly those having an articular head, with a biocompatible metal alloy stem and a head of brittle crystalline material, such as pyrocarbon-coated graphite. Such a combination is considered to have certain advantages because the properties of pyrocarbon can be tailored to more closely match properties of bone where an interface will occur, generally at an articulating surface. However, the differences between the structural properties of metal alloy stems and pyrocarbon-coated graphite heads pose a problem in designing such implants that can be effectively assembled and will have long lifetime. U.S. Pat. No. 6,997,958 recognizes the problem and proposes to limit the amount of tensile stress that may be applied to a head of brittle material when a Morse taper connection is employed; however, such a solution leaves the brittle head subjected to residual stress throughout its lifetime which may not be desirable. As a result, other solutions to this problem have continued to be sought.

SUMMARY OF THE INVENTION

A prosthetic implant for implantation at a biological joint utilizes an integral, one-piece polymeric insert to join a metal stem having a connector at one end to a head made of brittle crystalline material, particularly pyrocarbon-coated graphite. The head is formed with an entrance to an interior cavity of a size such that at least a portion of the polymeric insert must be elastically deformed to completely enter the cavity. The insert also has a cavity with an entrance region that is smaller than a corresponding dimension of an integral connector provided at the end of the metal alloy stem. The proportioning of the components is such that the polymeric insert preferably achieves an interference fit within the cavity of the pyrocarbon-coated head when mated, and the properties and dimensioning of the insert are such that it can also accommodate small tolerances in the thickness of a pyrocarbon-coated interior cavity of the head and yet produce a strong composite subassembly. The properties of the polymeric insert are chosen to accommodate the entry of the connector through the smaller entrance region by elastically deforming. Depending upon the ultimate arrangement desired, the proportioning may be such that the insert, upon return to its original physical configuration, may result in an interference fit at certain juxtaposed surfaces. Generally, the design will be such that, during assembly, the elastic limit of the polymeric material will not be exceeded so no significant plastic flow will occur; to facilitate the final mating of a subassembly of two components with the remaining component, i.e. either the metal alloy stem element or the brittle crystalline head, a circumferential relief region is provided. The stem can be designed with a neck of a specific length so that the head will either (a) seat on a flange that is a part of the stem or (b) pivot over a desired length of arc on a spherical connector at the end of the stem.

In a particular aspect, the invention provides a prosthetic implant for implantation into a resected bone, which implant comprises a metal stem element which has a connector at one end that is shaped with a reentrant region of reduced dimension, an integral one-piece polymeric insert which has a central cavity that receives said connector, and a head formed of brittle crystalline material having a central cavity being proportioned to receive said insert, said head cavity having an entrance of a size such that at least a portion of said polymeric insert must elastically deform inward to enter said cavity, said insert central cavity being formed with means for interengaging with said connector which requires radially outward deformation of at least a portion of said insert to lock said insert and said connector in engagement, and means providing a circumferential relief region into which a portion of said polymeric insert can elastically deform, and said integral polymeric insert being made of polymeric material having an elasticity, such that (a) it can deform radially inward sufficient to facilitate its entry into said head cavity and then return to shape, (b) it can deform radially outward to facilitate assembly with said connector and then return to shape, and (c) once assembled with both said head and said stem connector, disassembly cannot inadvertently occur, with said final assembly being facilitated by said relief region location.

In a more particular aspect, the invention provides a prosthetic implant for implantation into a resected bone at a joint, which implant comprises a metal stem element which has a connector at one end that is shaped with a reentrant region of reduced dimension, an integral one-piece polymeric insert which has an interior cavity that receives said connector and a flange that circumscribes an entrance to said cavity, and a head having an exterior articular surface and an interior cavity proportioned to receive said insert, said head being formed from a graphite substrate having interior and exterior pyrocarbon surfaces, said head cavity having an entrance formed by a reentrant entrance lip of a lesser inner diameter and a size such that said polymeric insert must elastically deform radially inward to enter said cavity, said polymeric insert cavity having an entrance region of a size smaller than said connector and having an outer groove which receives said head entrance lip and is proportioned to provide an annular gap in said groove, and said integral polymeric insert being made of polymeric material having an elasticity, such that (a) it can deform radially inward sufficient to facilitate its entry into said head cavity and return to shape, (b) its entrance region can deform radially outward to facilitate assembly with said connector, and (c) once assembled with both said head and said stem connector, disassembly cannot inadvertently occur.

In another particular aspect, the invention provides a method for forming a prosthetic implant, which method comprises providing a metal alloy stem element which has a connector at one end that is shaped with a region of reduced diametric dimension, providing a head of crystalline, brittle material having a cavity formed with an entrance of reduced diameter, providing an integral polymeric insert that is proportioned to seat within said cavity in said head, which insert has an interior central cavity that is proportioned to receive said connector at the end of said stem element and to interengage therewith at said connector region of reduced diametric dimension, forming a subassembly by mating said polymeric insert with said head by insertion of said insert through said entrance into said head cavity in a manner in which the polymeric material deforms elastically radially inward to facilitate its entry and returns to shape within said head cavity, and then completing said prosthetic implant by mating said subassembly with said stem element by inserting said connector into said interior cavity within said polymeric insert by causing said polymeric material to elastically deform radially outward at said interengaging means where it is accommodated by a circumferential relief region and then to return to a configuration having an interior diameter which thereafter prevents inadvertent disassembly of said head subassembly from said stem element.

BRIEF DESCRIPTION OF THE DRAWINGS

FIG. 1 is an exploded perspective view of the components of a prosthetic implant embodying various features of the invention.

FIG. 2 is an exploded view of the components of FIG. 1 in cross section.

FIG. 3 is a cross-sectional view similar to FIG. 2 showing a subassembly of the head and insert components.

FIG. 3A is an enlarged fragmentary view of a portion of the subassembly shown in FIG. 3.

FIG. 4 is a cross-sectional view of the complete assembly of the three components of FIG. 1.

FIG. 9 is an exploded perspective view of three components of a further alternative embodiment of a prosthetic implant embodying various features of the invention.

FIG. 10 is an assembled view of the components of FIG. 9 shown in cross-section.

FIG. 11 is a fragmentary cross-sectional view enlarged in size of a portion of FIG. 10 illustrating the interengagement between the components that make up the prosthetic implant.

DETAILED DESCRIPTION OF THE PREFERRED EMBODIMENTS

Figure 6:
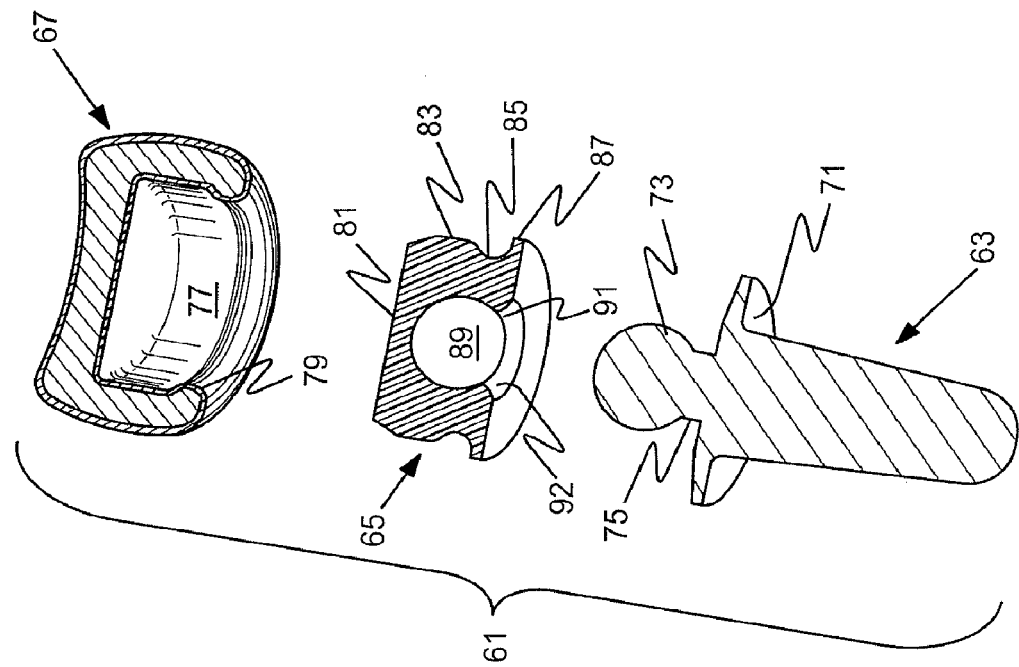
FIG. 6 is a view showing the exploded components of FIG. 5 in cross-section.
Figure 5:
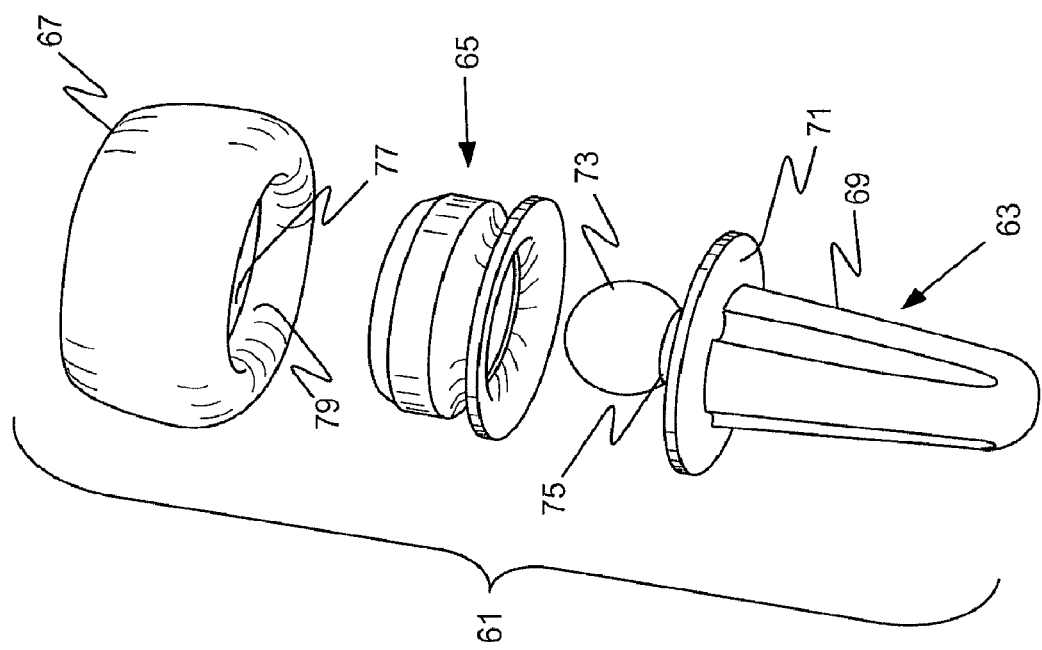
FIG. 5 is an exploded perspective view of the three components of an alternative embodiment of a prosthetic implant embodying various features of the invention.

Illustrated in FIGS. 1 through 4 is a prosthetic implant 11 designed to replace the proximal end portion of the radius. The implant 11 consists of three components: a metal alloy stem element 13, a plastic insert 15 and a head 17 of a brittle, crystalline, nonmetallic material, preferably a pyrocarbon-coated graphite substrate. When it is necessary to replace the proximal head of the radius for whatever reason, the implant provides an axisymmetric prosthesis similar to that shown in U.S. Pat. No. 6,217,616, entitled Elbow Prosthesis. By brittle is meant a crystalline material that fractures or fails instead of undergoing permanent deformation; such materials, although strong in compression, are inherently weak in tension.

The stem element 13 includes a stem portion 19 that is proportioned to be received in the medullary cavity of the resected radius. The stem portion may have any suitable cross-section, e.g. conical, cylindrical, polygonal or splined; it is designed to resist rotation relative to the radius once implantation has taken place. The radial axis is defined as the axis which passes through the proximal and distal heads of the radius. The stem element 13 is formed with a thin, circular flange 21 extending radially outward therefrom at a location intermediate its ends; the flange 21 defines the end of the implanted stem portion 19. When implanted, the undersurface of the flange 21 seats against the end surface of the resected radius. A connector 23 is constructed at the end of the stem, which is separated from the flange 21 by a neck 25 of reduced diameter. Although the flange 21, the connector 23 and the neck 25 are all circular in cross-section (when viewed in planes perpendicular to the axis of the stem), they could, if desired, be of polygonal or other suitable cross-section. The neck 25 thus provides a reentrant region between the flange 21 and the undersurface of the connector 23.

The stem element 13 is preferably machined from a strong, biocompatible, metal alloy. Materials such as titanium, stainless steel, and cobalt-chrome-molybdenum alloys that are biocompatible may be used. Such materials have the strength desirable to provide a strong replacement implant at a joint or the like where it will be subject to stresses.

The head 17 at the end of the implant will interface with the patient's native bones, and is made of a crystalline, nonmetallic material, e.g. a ceramic, which is inherently brittle. Although alumina and zirconia ceramics are very useful for many applications, it has been found that a dense pyrocarbon surface has superior properties for such an implant with an articular interface, and such is desirable and preferred. A dense, isotropic graphite substrate 31 that is coated with a uniform layer 33 of pyrocarbon continuously about its entire exterior surface is found to provide excellent performance. The pyrocarbon coating 33 should be at least about 200 microns thick for surfaces that will be subject to wear, preferably at least about 400 microns thick, and more preferably between about 500 and about 1000 microns thick. For surfaces where wear is not a factor, for example within a cavity where there is no relative motion, a coating thickness of about 50 microns or more should be adequate. During articulation of the elbow, the axial end of the head 17 of the illustrated insert 11 slides on the capitulum during flexion and extension of the elbow, and it generally rotates on the capitulum during pronation and supination of the forearm and hand. Moreover, the contact with the capitulum resists valgus forces applied to the arm, and also resists axial loads transmitted from the wrist to the elbow resulting from the gripping function of the hand. It is for this purpose that the axial end of the head 17 is provided with a shallow concave surface 27.

The lateral surface of the radius head is received in the radial notch that is formed in the medial portion of the ulna. The head 17 is formed with a generally barrel-shaped exterior surface 29 to interface well at the radial notch of the ulna. The head 17 of the radius is retained in this location at the elbow by the radial collateral ligament and the annular ligament of the radius. The annular ligament is attached to the ulna and is supported by the collateral ligament, which is in turn attached to the humerus, extending from a lateral region of the capitulum and being disposed about the head and over the annular ligament.

It has been found that pyrolytic carbon-coated, graphite substrates can be used to create prostheses having a modulus of elasticity within about 150% of the modulus of elasticity of natural bone; thus, this is considered to be a preferred material for manufacturing such prostheses. A particular pyrocarbon which is being marketed as On-X carbon (see U.S. Pat. No. 5,641,324) has advantageous properties for use in orthopedic prostheses such as these, particularly when such is coated upon a substrate of isotropic, fine grain graphite. The result is the creation of a strong radial component prosthesis which has excellent biomechanical properties. Because pyrocarbon is both physiologically inert and biochemically compatible with bone, and because the elastic modulus of such a pyrocarbon-coated graphite substrate is very close to that of cortical bone, such a prosthesis is highly biomechanically compatible and may be effectively used in such orthopedic implants, particularly those at joints within the human body where its articular surface is important. In addition to its highly compatible modulus of elasticity, pyrocarbon, and particularly On-X carbon, illustrates excellent wear characteristics at its interface with bone and also with cartilage, resulting in an implant which is highly bone compatible.

Consistent with the foregoing, the head 17 is made from a machined substrate of isotropic graphite 31 that is then coated with pyrocarbon in a fluidized bed coating apparatus, as known in this art, so as to provide a continuous pyrocarbon surface 33 about its entire exterior, as best seen in FIG. 2. To unite the pyrocarbon-coated graphite head 17 to the metal alloy stem 13 without the creation of substantial undesirable residual stresses, a carefully designed polymeric insert 15 is used, which is received in an interior central cavity 35 located in the head 17. The cavity 35 is axially aligned and includes an interior cylindrical wall 37 which is a surface of a right circular cylinder. The cavity 35 has an entrance 39 in the form of a reentrant arcuate lip of at least about 10% smaller diameter; it is designed to capture the peripheral portion of the polymeric insert 15 therewithin in a pocket created by the lip. Thus, the head 17 is very effectively joined to the insert 15, which is thereafter mated to the connector 23 at the end of the stem element 13.

The employment of a metal alloy stem for seating in the medullary cavity of the resected radius (or other such bone) and a pyrocarbon-coated graphite head for interfacing with and articulating with adjacent bones, e.g. the ulna and the humerus, allows one to take advantage of the preferred mechanical properties of both structural materials so long as a satisfactory arrangement mating the metallic stem and the crystalline head can be effectively and efficiently provided. It is in this respect that the polymeric insert 15 is designed and used; it is designed to take into consideration the relative stiffness and Young's Modulus of each of these two diverse materials, and particularly the brittleness of isotropic crystalline graphite, and effectively mate the two materials. Dimensioning is such that a residual strain on the head 17 of less than 10% of fracture strain can be achieved. Moreover, it can be appreciated that the pyrocarbon coating of graphite substrates which is carried out in a fluidized bed coater, such as that taught in U.S. Pat. No. 6,410,087, requires precise control, and coating both the exterior and the interior surfaces in a component, such as the graphite substrate 31 for the head 17, poses particular problems from the standpoint of tolerances. The thickness of the coating of the exterior surfaces that will be subject to wear is regulated to achieve the preferences previously set forth; the coating may be of somewhat lesser thickness upon interior surfaces that are not subject to wear. It has been found, however, that the use of an ultrahigh molecular weight polyethylene (UHMWPE) of a density of about 0.94 gm/cm$^3$, and meeting ASTM Standard F648, allows an insert to be designed that will effectively join one to the other and create a strong interference fit between the two without requiring close coating tolerances to be held for the interior wall surfaces of the cavity 35 in the graphite substrate and while still respecting the brittleness of graphite. Such UHMWPE will have a tensile modulus of about 100,000 psi; it will prevent subsequent disassembly, particularly when the desired interference fit is achieved by appropriately proportioning the components.

As best seen in FIG. 2, the polymeric insert is formed with an exterior lateral surface or wall 41 that is shaped to juxtapose with and, if desired, create a low stress interference fit against the interior wall surface 37 in the pocket within the pyrocarbon head 17. The upper end of the lateral wall of the insert is chamfered to provide a tapered surface 43, and the lower exterior region of the insert is constructed with a neck defined by a circumferential groove 45 located just above a circular bottom flange 47, which has a flat undersurface that is designed to juxtapose with the upper surface of the flange 21 of the stem element, seating fairly tightly against it if desired. In the illustrated construction, the inward protruding entrance lip 39 to the cavity 35 in the pyrocarbon head 17 is a convex surface section of a torus, and the exterior circumferential groove 45 in the insert is a similarly shaped section of a concave toroidal surface providing a hollow region. The dimensioning is such that an annular gap 48 of crescent shape in cross-section is provided between the facing toroidal surfaces in the head/insert subassembly, which serves as a relief region as described hereinafter. In the illustrated embodiment, the upper end of the insert has an optional opening 49 at the top; however, alternatively, its upper end it could be closed if desired.

The polymeric insert 15 has an interior cavity 51 that is designed to receive and mate with the exterior surface of the connector 23 at the end of the stem element. In the embodiment shown, the insert cavity 51 has an interior, right circular, cylindrical surface 53 proportioned to mate with the surface of the same shape that forms the lateral exterior of the connector 23. The polymeric insert 15 is formed with an entrance region 55 at its lower end having an upwardly and inwardly tapered surface. The entrance region 55 terminates with an annular locking ring 57 that will, when mated with the connector 23, interengage or seat against an annular undersurface 59 that is formed on the connector 23 of the stem element at the location where it meets the neck 25. The diameter of the cavity 51 is preferably at least about 5% greater than the inner diameter of the locking ring 57 located at the upper end of entrance 55. The specific properties of each of these components will be better understood through the following description as to how the insert 11 is assembled from these three components.

The implant 11 is illustrated in FIG. 3 with the stem element 13 spaced from a subassembly wherein the insert 15 has been mated with the pyrocarbon-coated head 17. The subassembly depicted in FIG. 3 is simply achieved by relative movement of the head 17 and the insert 15 along the central axis. There is initial engagement between the tapered chamfer surface 43 and the reentrant arcuate entrance lip 39 leading to the cavity of the head 17. The UHMWPE material chosen for the insert 15 has sufficient elasticity that allows it to be gradually radially inwardly compressed as the hollow insert passes through the reduced circular region of the entrance lip 39; the components are appropriately sized so that the elastic limit of the polymer is not exceeded. Once in place within the pocket provided in the head cavity 35, the polymeric insert returns to its original dimensions, and if desired, it may effect an interference fit between the juxtaposed surfaces 41 and 37. The arcuate entrance lip 39 leading to the head cavity 35 is seated snugly in the hollow of the exterior groove 45 in the polymeric insert which pinches against it along two axially spaced circular regions, as seen in FIG. 3A. The proportioning is such as to leave an annular gap or region 48 of crescent-shaped cross-section which serves a relief purpose described hereinafter. This seating, along with any interference fit between the two cylindrical surfaces, locks the subassembly components in tight interengagement. Interfitting and tight interengagement provides a strong composite head; the physical character of the polymeric material of the insert combines with the physical character of pyrocarbon-coated graphite to provide a composite head which exhibits improved overall strength and physical properties, compared to an inherently brittle, pyrocarbon-coated graphite head. The polymeric insert 15 can preferentially absorb shock and insulate the head from possible fracture, and it can also cushion loading at the joint that would otherwise directly stress the pyrocarbon-coated graphite.

Once the subassembly is completed, subsequent relative axial movement to interengage the subassembly and the stem element 13 produces the complete assembly shown in FIG. 4. As these two components are moved into engagement with each other, the peripheral, upper edge of the connector 23 which is rounded, e.g. arcuate, contacts the tapered surface entrance surface 55 of the insert 15, and as relative movement continues, the polymeric material is deformed radially outward from forces acting in a radially outward direction, squeezing it toward the surrounding annular lip portion of the confining pyrocarbon-coated head 17. It is here that the value of the annular relief gap 48 plays its part. To avoid the elastic limit of the UHMWPE polymer being exceeded in the region of the locking ring 57, as a result of rigid confinement between the surrounding annular reentrant lip 39 of the head 17 and the transiting cylindrical surface of the connector 23, the relief gap 48 is sized to accommodate an adequate amount of elastic movement in the wall of the insert in this region and should be of a volume of at least about 90% of that of the locking ring. This circumferential relief avoids any significant plastic flow of the polymer as the larger diameter connector 23 passes therethrough which preserves the contour of the locking ring 57 to assure an ultimate locking fit of it and the undersurface flange 59 of the connector 23.

Once the passage is complete, the flat undersurface of the flange 47 at the bottom of the insert has become juxtaposed with the upper surface of the circular flange 21 of the stem, and the connector 23 is seated in the mating cavity 51 of the insert. In this position, the locking ring 57, which has been preserved as a result of the presence of the relief gap 48, is juxtaposed with the facing annular undersurface 59 of the connector, where it meets the neck, so that the connector 23 of the stem cannot be withdrawn from the overall assembly without deforming the locking ring portion of the entrance region of the polymeric insert. To attempt disassembly, it would be necessary to grasp both the implantable stem portion 19 and the head 17 and try to axially pull them apart; it can be seen that such movement would be strongly resisted by the juxtaposed ring 57 and undersurfaces 59. The at least 10% difference in diameter between the reentrant lip 39 and the outer diameter of the insert 15 prevents their disassembly without destruction of one component of the subassembly. Thus, it can be seen that a very secure connection is achieved.

Because the proportioning of the interior cavity 51 of the polymeric insert and the exterior surface of the connector 23 can be held to close tolerances, any desired relationship can be reasonably attained. For example, the dimensioning can be such, as described above, that an interference fit is achieved between the lateral surface of the connector 23 and the interior surface of the insert cavity 51. Alternatively, if it is desired to allow relative rotation of the head 17 on the end of the stem 13, the proportioning could be such that there would be sufficient clearance between the exterior surface of the connector 23 and the interior facing surfaces of the polymeric insert cavity that rotational movement about the axis would be permitted. In this case, the entrance region 55 would be sized so that it would permit rotation about the interface between the entrance region flange 47 and the flange surface 21 of the stem element 13.

Illustrated in FIGS. 5 through 8 is an alternative embodiment showing an implant 61 where the attitude of the head may be allowed to vary slightly with respect to the axis of the stem. The implant 61 again consists of an assembly of three components, a metal stem element 63, a polymeric insert 65 and a pyrocarbon-coated graphite head 67. As described previously, the metal alloy stem element 63 includes an implantable stem portion 69, a circular flange 71 and a connector 73, which in this embodiment is a section of a sphere, that surmounts a neck 75. The spherical surface of the connector 73 is at least about 10% greater than that of a hemisphere, and preferably at least about 40% greater and more preferably at least about 80% of the surface of a sphere.

The head 67 is essentially the same as the head 17 described hereinbefore; it is an isotropic graphite substrate that is coated with a continuous coating of pyrocarbon having a thickness of at least about 200 microns across its entire exterior surface. The pyrocarbon coating is continuous so as to cover the walls of its interior cavity 77, entry to which cavity is through a similar entrance having a reentrant lip 79. Similarly, the exterior lateral surface of the polymeric insert 65 is again essentially the same as heretofore described. However, this polymeric insert has a flat upper surface 81, which is juxtaposed with the flat interior surface that forms the upper end of the cavity 77 in the head, and it has a cylindrical, lateral wall 83, which is received in the pocket in the head and proportioned to juxtapose with and, if desired, form an interference fit within the mating, pyrocarbon-coated, interior lateral surface of the cavity 77. The polymeric insert 65 likewise has a circumferential groove or hollow 85 which receives the reduced diameter reentrant lip 79 of the head, which groove 85 is located just above a circular flange 87 at the bottom of the insert. It is proportioned to leave an annular relief gap 88 similar to the gap 48 of crescent shape cross-section.

The major difference lies in that the interior cavity 89 of the insert is spherical so as to mate with the spherical connector 73 at the end of the stem element 63. As best seen in FIG. 7, the cavity 89 again has an annular arcuate entrance 91 of reduced diameter leading into the spherical cavity; the cavity 89, if cut by an axial plane, would subtend an arc of at least about 220° and preferably at least about 240°, e.g. between about 240° and 250°, which assures locking the connector 73 within the head subassembly. The annular entrance 91 of the insert is shaped to provide a tapered lead-in surface 92. It may be arcuate as illustrated, e.g. a section of the surface of a torus, or it may be a section of a cone. The circular edge where the entrance meets the cavity 89 is preferably slightly rounded, e.g. a radius of about 0.020 in. (0.5 mm) might be used.

Figure 7:
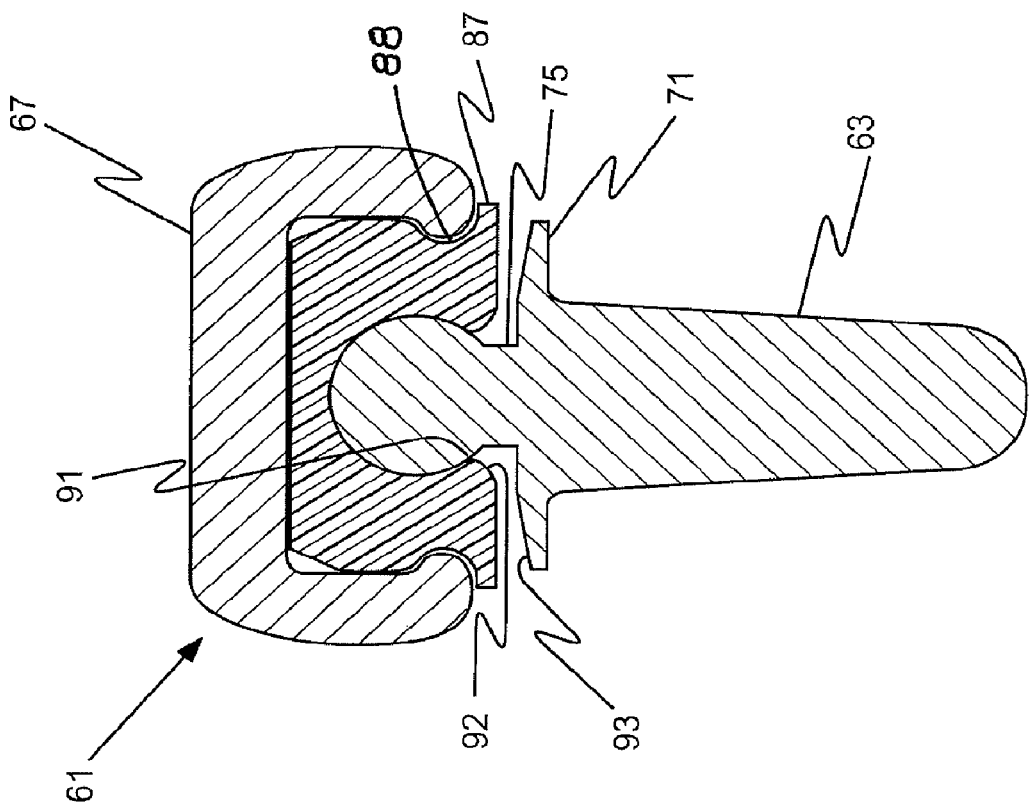
FIG. 7 is a cross-sectional view of the assembled three components of FIG. 5.

A further difference in the construction of the implant 61 is that it is constructed so as to be bi-polar, a term used in orthopedics to indicate that the attitude of the head 67 can be varied relative to the axis of the implant. To achieve such construction, the stem element has a neck 75 that is elongated, relative to the neck 25, so that, as seen in FIG. 7, the undersurface of the flange 87 at the bottom of the insert is spaced apart from the flange 71 of the stem 63 when the head is aligned coaxially with the stem. Moreover, the upper surface of the flange 71 on the stem element is preferably shaped to have a peripheral frustoconical surface region 93.

Figure 8:
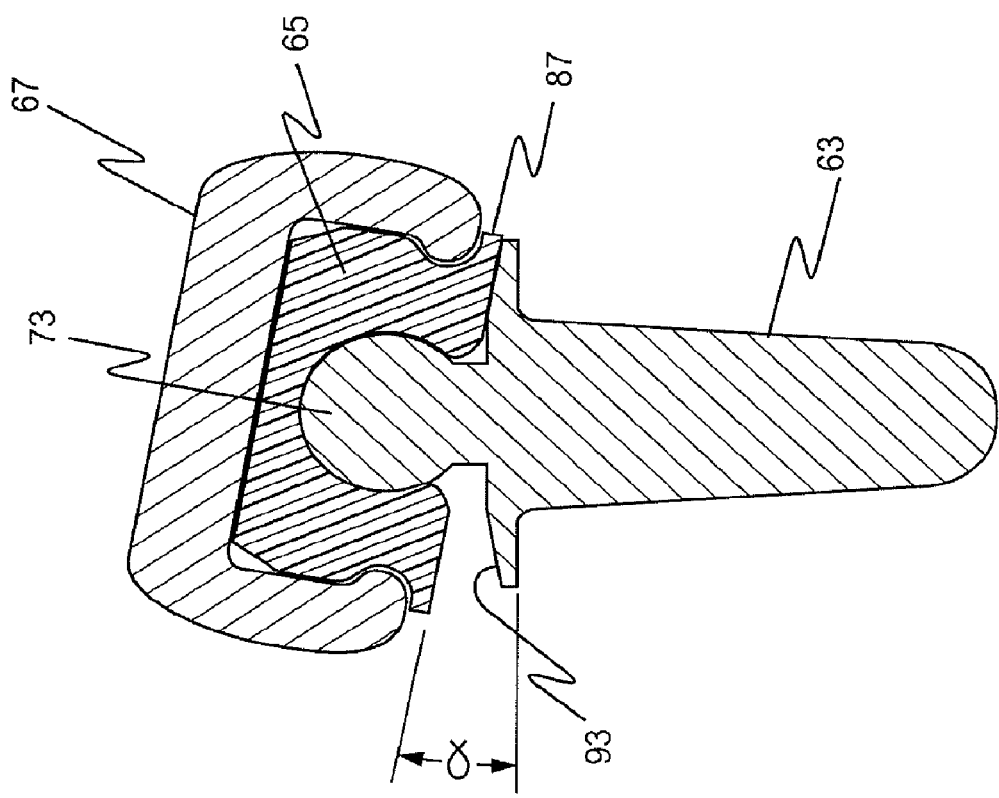
FIG. 8 is a cross-sectional view similar to FIG. 7 with the head pivoted with respect to the stem.

Accordingly, the head 67 of the insert 61, as a result of the spherical connector 73 and the elongated neck 75, can change in attitude by pivoting along an arc in any direction; moreover, it can rotate on the connector. Generally, the amount of pivoting allowed, from the coaxial alignment shown in FIG. 7, in one direction in the axial plane of the implant will be limited to the extent of about 5-15°. Comparison of FIGS. 7 and 8 shows such maximum pivoting in one direction by an arc of the angle α; preferably, the pivoting allowed is not greater than about 10°. When pivoting to the full extent is achieved, as depicted in FIG. 8, the flat undersurface of the flange 87 of the insert 65 smoothly abuts the frustoconical surface portion 93 of the stem.

Assembly of these components is essentially as hereinbefore described. Initial relative movement between the polymeric insert 65 and the head 67 causes the insert to elastically, radially inwardly deform and then expand to its original shape and, if desired, form an interference fit once fully within the pocket provided in the cavity 77 of the head. Subsequent relative axial movement between this subassembly and the stem element 63 causes the spherical connector 73 to pass through the reduced diameter entrance 91, deforming the polymeric material of the insert 65 in a radially outward direction; the presence of the circumferential relief provided by the gap 88 accommodates such deflection in the region of entrance ring portion to assure that stress upon the polymeric material remains within its elastic limits Then the entrance region elastically snaps back into place, with the ball connector 73 seated in the spherical cavity 89 of the insert. By proportioning the relief gap 88 to be of sufficient size and the curved entrance region of the region so that its diameter is between about 70% and 85% of the diameter of the sphere, and preferably about 75%±3%, it is assured that assembly can be readily achieved and that inadvertent disassembly of the components of the implant 61 cannot occur once assembled; moreover, plastic flow of the chosen UHMWPE will not occur during assembly. Thus, the illustrated arrangement not only provides effective joinder between a somewhat brittle pyrocarbon-coated graphite insert and a metal stem, but it also results in a strengthened composite unit which is bi-polar, i.e. allowing a change in attitude of as much as angle α of arc in any direction from a coaxial attitude where flange 87 of the insert 65 is perpendicular to the axis of the stem element 63.

Illustrated in FIGS. 9, 10 and 11 is another alternative embodiment showing an implant 111 which, from its exterior appearance (FIG. 10), closely resembles the implant 11; however, the design of the polymeric insert and its interengagement with the connector of the stem element is different, while the pyrocarbon-coated head is only slightly different. The implant 111 consists of an assembly of three components: a metal stem element 113, a polymeric insert 115, and a pyrocarbon-coated graphite head 117. As described previously, the metal alloy stem element 113 includes an implantable stem portion 119, a circular flange 121, and a connector 123 which resembles the connector 23, being separated from the flange by a short neck 125. However, it includes a circumferential groove 126 which cooperates in the interengagement with the polymeric insert 115.

The head 117 is essentially the same as the head 17 as described hereinbefore; it is an isotropic graphite substrate that is coated with a continuous coating of pyrocarbon having a thickness of at least about 200 microns across the shallow, concave surface 127 at its axial end and the lateral exterior surface 129. The carbon coating is continuous so as to cover the wall surface of an interior cavity 131 has a lateral interior wall 133 of right circular cylindrical shape 133 that terminates in a pair of transitional surfaces 135a and 135b which lead to the flat upper wall of the cavity and to the reentrant lip 137 which forms the entrance to the cavity 131 of lesser diameter than the lateral wall surface 133.

In this embodiment, the polymeric insert 115 is in the shape of a sleeve which fits entirely within the confines of the pyrocarbon-coated head 117. It is again formed from a suitable polymeric material, preferably UHMWPE, having suitable elastic properties as described hereinbefore. The sleeve is formed with a lateral surface 141 that is a surface formed by two spaced apart sections of a right circular cylinder that terminates in a pair of transitional surfaces 143a and 143b that match the shape of the surfaces 135a and b on the interior cavity of the pyrocarbon head and are juxtaposed therewith when assembled. The lateral surface 141 is interrupted by a central annular groove or hollow 145 which serves as a relief region as described hereinafter. The sleeve has an interior surface 147, which is also that of a right circular cylinder and provides a central cavity to receive the connector 123, from which surface there is a central protruding circumferential locking flange 149 of arcuate shape that serves to cause interengagement of the polymeric insert 115 and the connector 123 at the head of the stem element.

The circumferential groove 126 in the connector 123 is formed with a depth (H2 in FIG. 11) so as to receive the circumferential flange 149 of the insert and with a pair of parallel radial walls 151 that transition between its outer cylindrical surface 123 and the base of the groove. The walls 151 are spaced apart by the distance WI in FIG. 11.

A subassembly of the pyrocarbon-coated graphite head 117 and the polymeric insert 115 is first made, as previously described, by relative movement of the two so that the insert enters through the narrowed entrance provided by the protruding lip 137. The arcuate transitional surface 143a, at the end of the insert, serves as a tapered lead-in surface that begins the radially inward elastic deformation of the generally tubular insert 115 as it moves past the narrower diameter of the lip 137. Once fully in place within the cavity 131 of the head, it returns to its original shape. The insert is preferably proportioned so as to create an interference fit with the lateral surface 133 of the cavity of the head, with the two transitional surfaces 143a and b juxtaposing with the facing surfaces 135a and b of the head cavity.

Next, relative movement between the stem element 113 and the subassembly causes the connector 126 to slide past the pyrocarbon lip 137 where some very slight clearance is provided and to likewise slide through the initial section of the interior cavity surface 147 of the insert, until a chamfered lead-in section 155 at the end of the connector engages the protruding circumferential flange 149 of the insert. At this point, the middle region of the confined polymeric insert 115 is forced radially outward in elastic deformation by the lateral surface 123 of the connector. However, the relief region provided by the annular groove or hollow 145, that is at the same axial location as the protruding locking flange 149, provides a region into which the polymeric material can move without undergoing plastic flow and again should have a volume at least about 90% of that of the protruding flange. Further insertion of the stem element 113 completes the assembly when the circumferential flange of the polymeric insert is seated in the circumferential groove 126 of the stem connector, as depicted in FIG. 11. Proportioning is preferably such that the width of the protruding flange 149 is about the same as the dimension WI of the groove 126, and that the depth H1 of the relief groove 145 is about the same as the thickness H2 of the protruding flange (which is about equal to the depth of the connector groove 126). As can be seen in this FIGURE, the interengagement of the circumferential flange 149 within the groove 126, with the sharp corners of the groove wall 151 seated at opposite ends of the circumferential protruding flange 149, creates a tight locking engagement so that inadvertent disassembly is no longer possible.

Although the invention has been described with regard to certain preferred embodiments which constitute the best most presently known for constructing the invention, it should be understood that various changes and modifications may be made without departing from the scope of the invention, which is set forth in the claims appended hereto. Although the illustrated prostheses all illustrate an implant where the axis of the head is coaxial with the axis of the stem, it should be clear that this is not a requirement and that the head for a metacarpal phalangeal joint, for example, which might be preferably at an angle to the axis of the stem, could utilize the same assembly arrangement as illustrated herein. Likewise, it is not a requirement that the pyrocarbon head be closed at its top; a head could be more in the form of a sleeve from which the end of the stem element would protrude; head surface character is simply dictated by the desired articular surface of the resultant implant. Moreover, the stem element need not include a circumferential flange, although such is preferred as it provides a positive location for placement of the implant in the bone being repaired. Although the head for the implant is described as preferably being made from pyrocarbon-coated, isotropic graphite, particularly when the implant is to be used at a location where there is articulation, the invention is also advantageous for the assembly of other crystalline, nonmetallic brittle material heads to a metal stem, for example, ceramic heads that likewise are brittler and have significant differences in physical properties from metal alloy stems. Accordingly, the method of forming a composite implant, including a high tensile strength metal alloy stem element and a crystalline, brittle head, particularly one having an articular surface, opens up the opportunity for prosthesis design to take advantage of desired features of materials for both head and stem construction. Moreover, the method of joinder of two such components of differing physical properties that, in addition, enhances the operational character of the head and renders the method particularly valuable. There may also be variations in the cross-sectional geometry of the polymeric insert circumferential flange; instead of the flange having a cross-section of a circle, other suitable cross-sections may be used, e.g. trapezoidal or triangular. It is also possible to reverse the interference snap lock mechanism so that the polymeric insert is first assembled on the metal stem component to form the initial subassembly. This subassembly would then be inserted into the head cavity, with the arrangement being such that a radially outwardly protruding circumferential flange is radially inwardly deformed until it reaches an appropriately shaped groove or pocket located in the interior wall of the head component, where the flange snaps outward into a locking interengagement.

Particular features of the invention are emphasized in the claims which follow.

The invention claimed is:

1. A prosthetic implant for implantation into a resected bone, which implant comprises:
    a metal stem element which has a connector at one end that is shaped with a reentrant region of reduced dimension,
    an integral one-piece polymeric insert which has a central cavity that receives said connector,
    a head formed of brittle crystalline material having a central cavity being proportioned to receive said insert, said head having a concave articular surface which will interface with the patient's native bones
    said head cavity having an entrance of a size such that at least a portion of said polymeric insert must elastically deform inward to enter said cavity,
    said insert being formed with means for interengaging with said connector which requires radially outward deformation of at least a portion of said insert to lock said insert and said connector in engagement, and
    means providing a circumferential relief region into which said portion of said polymeric insert can elastically deform to facilitate final assembly,
    said integral polymeric insert being made of polymeric material having an elasticity, such that (a) it can deform radially inward sufficient to facilitate its entry into said head cavity and then return to shape, (b) it can deform radially outward to facilitate assembly with said connector and then return to shape, and (c) once assembled with both said head and said stem connector, disassembly cannot inadvertently occur.

2. The implant of claim 1 wherein said polymeric insert has an exterior lateral cylindrical wall of circular cross-section and a tapered end region to facilitate its entry into said entrance of said head cavity, which entrance is defined by an inwardly protruding lip.

3. The implant of claim 2 wherein said stem element has a radial flange of generally circular shape located between an implantable stem portion of said metal stem element that is of lesser diameter and said connector, which flange has an undersurface that seats against the resected bone.

4. The implant of claim 3 wherein said connector is joined to the remainder of said metal stem element by a neck portion of reduced dimension which extends from said radial flange.

5. The implant of claim 4 wherein said diameter of said polymeric insert cavity is such that assembly of said stem connector and said insert creates an interference fit between said connector and said surface of said polymeric insert cavity.

6. The implant of claim 5 wherein said polymeric insert has an entrance region leading to said insert cavity and said cavity and said entrance region are both of circular cross-section, with said cavity having a diameter that is at least about 5% greater than the diameter of said circular entrance.

7. The implant of claim 6 wherein said polymeric insert has an exterior neck of a diameter less than that of its cylindrical outer wall surface, which neck is located adjacent to an outwardly extending flange surrounding said entrance region.

8. The implant of claim 7 wherein said head has a reentrant lip that forms said entrance into said head cavity, which lip has a convex annular surface, and wherein said insert exterior neck is formed by a groove with a concave annular surface that receives said lip and leaves an annular gap that provides said relief region which accommodates elastic deformation of said polymeric insert when said stem element is assembled with a subassembly of said head and said polymeric insert.

9. The implant of claim 8 wherein said lip and said groove have toroidal surfaces and a crescent-shaped gap therebetween provides said relief region.

10. The implant of claim 8 wherein said neck portion of said stem element has a length such that, with said head, said insert and said stem element assembled to one another, said flange of said insert is juxtaposed with said flange of said stem.

11. The implant of claim 2 wherein said head is made of graphite, all of the surfaces of which are coated with a continuous coating of pyrocarbon, said head cavity and said insert have matching cylindrical surfaces, and the diameter of said cylindrical outer surface of said polymeric insert is such that assembly of said insert within said head creates an interference fit at said cylindrical surfaces.

12. The implant of claim 11 wherein said polymeric insert is made of ultrahigh molecular weight polyethylene which meets ASTM Standard F648.

13. A prosthetic implant for implantation into a resected bone at a joint, which implant comprises:
   a metal stem element which has a connector at one end that is shaped with a reentrant region of reduced dimension,
   an integral one-piece polymeric insert which has an interior cavity that receives said connector and a flange that circumscribes an entrance to said cavity, and
   a head having an exterior articular surface and an interior cavity of circular cross section proportioned to receive said insert, said head being formed from a graphite substrate having interior and exterior pyrocarbon surfaces,
   said head cavity having an entrance formed by a reentrant entrance lip of a lesser inner diameter than said head cavity and a size such that said polymeric insert must elastically deform radially inward to enter said cavity,
   said polymeric insert cavity having an entrance region of a size smaller than said connector and having an outer groove which receives said head entrance lip and is proportioned so that an annular relief region remains in said groove when said insert is assembled with said head, and
   said integral polymeric insert being made of polymeric material having an elasticity, such that (a) it can deform radially inward sufficient to facilitate its entry into said head cavity and return to shape, (b) its entrance region can deform radially outward to facilitate assembly with said connector, and (c) once assembled with both said head and said stem connector, disassembly cannot inadvertently occur.

14. A prosthetic implant for implantation into a resected bone, which implant comprises:
   a metal stem element which has a connector at one end that is shaped with a right circular cylindrical lateral surface and with a reentrant region of reduced dimension,
   a head having a surface to articulate with native bone, which head is formed of brittle crystalline material and has a central cavity proportioned to receive a polymeric insert cavity,
   an integral one-piece polymeric insert which has a central cavity that receives said connector and that is formed with a right circular cylindrical interior surface to juxtapose with said connector lateral surface,
   said head central cavity having an entrance in the form of an inwardly protruding lip of a size such that at least a portion of said polymeric insert must elastically deform inward to enter said cavity,
   said polymeric insert being formed with means for interengaging with said connector which means requires radially outward deformation of at least a portion of said insert to lock said insert and said connector in engagement, and
   means providing a circumferential relief region between said lip of said head and said insert into which said portion of said polymeric insert can elastically deform to facilitate final assembly,
   said integral polymeric insert being made of polymeric material having an elasticity such that (a) it can deform radially inward sufficient to facilitate its entry into said head cavity and then return to shape, (b) it can deform radially outward to facilitate assembly with said connector and then return to shape, and (c) once assembled with both said head and said stem connector, disassembly cannot inadvertently occur.

* * * * *